United States Patent [19]

Hoeschele et al.

[11] Patent Number: 4,999,444

[45] Date of Patent: Mar. 12, 1991

[54] NOVEL NEUTRAL MIXED LIGAND PLATINUM(II) AND PLATINUM(IV) COMPLEXES

[75] Inventors: James D. Hoeschele, Canton; Leslie M. Werbel, Ann Arbor, both of Mich.

[73] Assignee: Warner-Lambert Co., Morris Plains, N.J.

[21] Appl. No.: 321,818

[22] Filed: Mar. 10, 1989

[51] Int. Cl.$^5$ .................... C07F 15/00; A01N 55/02; A61K 31/28
[52] U.S. Cl. .................................................. 556/137
[58] Field of Search .................. 514/492; 556/137

[56] References Cited

U.S. PATENT DOCUMENTS 4,169,846 10/1979 Kidani et al. .

FOREIGN PATENT DOCUMENTS 0098121 6/1983 European Pat. Off. .
0237450 3/1987 European Pat. Off. .
63-17894 1/1988 Japan .

OTHER PUBLICATIONS

CA 109; 102241r of Zhu et al., *Jiegou Huaxue 1987*, 6(4), 240-9.
J. Med. Chem. 1987, 30, 1327-1336.

*Primary Examiner*—Paul F. Shaver
*Attorney, Agent, or Firm*—Franics J. Tinney

[57] ABSTRACT

Novel cyclodiamineplatinum(II) and platinum(IV) complexes which are useful in inhibiting the growth of malignant neoplasms, as well as novel pharmaceutical compositions and methods of use, as well as processes for their manufacture are herein described.

6 Claims, No Drawings

NOVEL NEUTRAL MIXED LIGAND PLATINUM(II) AND PLATINUM(IV) COMPLEXES

BACKGROUND OF THE INVENTION

The present invention relates to novel neutral mixed ligand platinum(II) and platinum(IV) complexes useful as pharmaceutical agents, to methods for their production, to pharmaceutical compositions which include these compounds and a pharmaceutically acceptable carrier, and to a pharmaceutical method of treatment. More particularly, the novel complexes of the present invention are active against the L1210 and P388 murine leukemia cell lines, thus inhibiting the growth of malignant neoplasms in mammals.

Various platinum compounds have been shown to possess antitumor activity. This has been highlighted by the clinical utility of cisplatin (A)

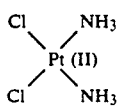 A in the treatment of human tumors. However, because of the severe toxicity, especially nephrotoxicity, associated with the therapeutic use of cisplatin, a number of additional platinum(II) and platinum(IV) analogs have been synthesized and evaluated for antitumor activity. Thus, U.S. Pat. No. 4,169,846 discloses platinum(II) complexes which exhibit antitumor activity in mice of formula

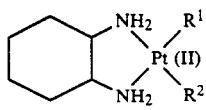

wherein the stereoisomerism of 1,2-diaminocyclohexane is cis-, trans-d-, or trans-l; and $R^1$ and $R^2$ represent the same halogen atoms, or $R^1$ and $R^2$ may, when taken together, form a group represented by the formula

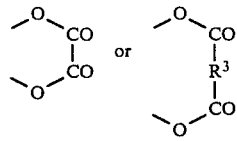

where $R^3$ represents a $>CH_2$ group, a $>CHCH_3$ or $>CHCH_2CH_3$ group. Further, it relates to complexes of uracil and cis[platinum(II)-cis, trans-d-, or trans-l-1,2-diaminocyclohexane].

European Patent Application 0098121 discloses platinum(II) complexes which exhibit antitumor activity in mice of formula

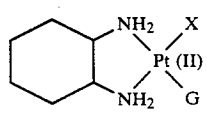

wherein X is a halogen atom and G is a glucuronic acid residue.

Witiak, D. T., et al., *Journal of Medicinal Chemistry*, 30, pages 1327–1336 (1987) reported the synthesis and antitumor evaluation of a series of diastereomeric 1,2-dihydroxy-4,5-diaminocyclohexane platinum(II) complexes.

European Patent Application 0237450 discloses platinum(IV) complexes which exhibit antineoplastic or antitumor activity of formula

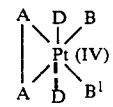

wherein the moiety

denotes a 1,2-cyclohexanediamine ligand of the formula:

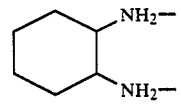

where the 1- and 2-amino groups show a configuration selected from cis-, trans-l- and trans-d- relative to the cyclohexane ring, or the moiety

denotes a (aminomethyl)cyclohexylamine ligand of the formula where the 1-amino group and 2-aminomethyl group show a configuration selected from cis-l-, cis-d-, trans-l- and trans-d-, or a mixture thereof relative to the cyclohexane ring; B and B' taken together with the platinum atom form a ring of the formula

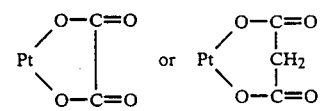

Japanese Patent Application 63-17,894 discloses a series of cis-diaminocyclohexanolplatinum complexes represented by any of the general formulas:

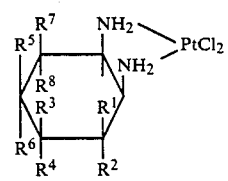

(B)

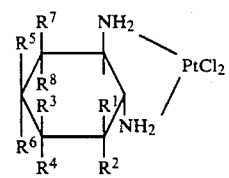

(C)

-continued

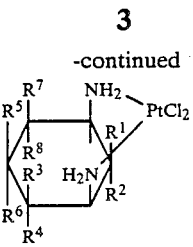

(D)

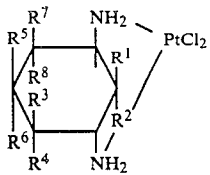

(E)

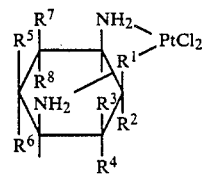

(F)

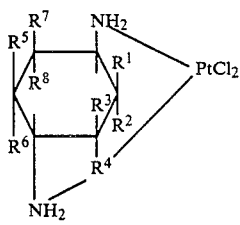

(G)

wherein $R^1$–$R^8$ stand for a hydrogen atom or a hydroxyl group. These hydroxyl-containing diaminocyclohexane derivative were disclosed as exhibiting antitumor activity.

However, the previous complexes of platinum(II) and platinum(IV) suffer the drawbacks of inadequate water solubility and/or an unacceptable therapeutic index. Additionally, in the previous known platinum complexes of 1,2-diaminocyclohexane (DACH) the cyclohexane ring can assume a normal chair configuration. In contrast, the compounds of the present invention, in particular the 1,4-diaminocyclohexane (DACH) derivatives, are structurally unique in that the cyclohexane ring is constrained to a boat configuration. This appears to be the first example of this type of structural novelty in coordination chemistry. Thus, we have found unexpectedly that the platinum(II) and platinum(IV) complexes of the present invention have increased water solubility and antineoplastic activity over the compounds of the prior art.

SUMMARY OF THE INVENTION

Accordingly, a first aspect of the present invention is a neutral mixed ligand platinum (II) complex of Formula I

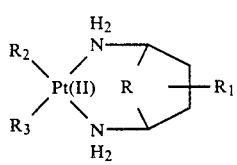

or a pharmaceutically acceptable acid addition salt thereof, wherein R is oxygen,

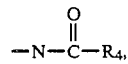

in which $R_4$ is an alkyl group of from one to ten carbon atoms, or

—$(CH_2)_n$—, in which n is an integer from one to three;

$R_1$ is hydrogen, carboxyl, an alkyl group of from one to four carbon atoms, an alkyl group of from one to four carbon atoms substituted with alkoxy of from one to four carbon atoms, a cycloalkyl group of from three to six carbon atoms, a hydroxyalkyl group of from one to four carbon atoms, an alkoxy group of from one to four carbon atoms, or benzyl; and $R_2$ and $R_3$ are negatively charged monodentate ligands which may be the same or different and are selected from the group consisting of chloro, bromo, iodo, nitrato, and acetato or $R_2$ and $R_3$ taken together form a dinegatively charged bidentate ligand selected from the group consisting of sulfato, oxalato,

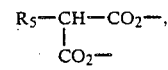

in which $R_5$ is hydrogen, hydroxyl, amino, an alkyl group of from one to four carbon atoms, or an aminoalkyl group of from one to four carbon atoms,

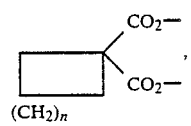

in which n is an integer from one to three, and

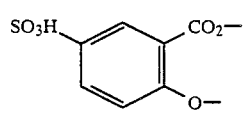

A second aspect of the present invention is a neutral mixed ligand platinum(IV) complex of Formula II

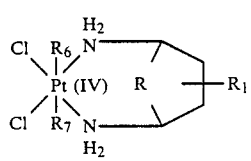

or a pharmaceutically acceptable acid addition salt thereof, wherein R is oxygen,

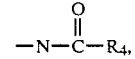

in which $R_4$ is an alkyl group of from one to ten carbon atoms, or

—$(CH_2)_n$—, in which n is an integer from one to three;

$R_1$ is hydrogen, carboxyl, an alkyl group of from one to four carbon atoms, an alkyl group of from one to four carbon atoms substituted with alkoxy of from one to four carbon atoms, a cycloalkyl group of from three to six carbon atoms, a hydroxyalkyl group of from one to four carbon atoms, an alkoxy group of from one to four carbon atoms, or benzyl; and $R_6$ and $R_7$ are negatively charged monodentate ligands which may be the same or different and are selected from the group consisting of chloro, bromo, hydroxyl, and nitrato.

Additionally, the present invention is directed to a pharmaceutical composition for inhibiting the growth of neoplasms in mammals comprising an antineoplastically effective amount of a neutral mixed ligand platinum(II) complex of Formula I as defined above in combination with a pharmaceutically acceptable carrier.

Also, the present invention is directed to a novel method of inhibiting the growth of neoplasms in mammals comprising administering to said mammal an effective amount of a neutral mixed ligand platinum(II) complex of Formula I as defined above in combination with a pharmaceutically acceptable carrier.

Further, the present invention is directed to a pharmaceutical composition for inhibiting the growth of neoplasms in mammals comprising an antineoplastically effective amount of a neutral mixed ligand platinum(IV) complex of Formula II as defined above in combination with a pharmaceutically acceptable carrier.

Also, the present invention is directed to a novel method of inhibiting the growth of neoplasms in mammals comprising administering to said mammal an effective amount of a neutral mixed ligand platinum(IV) complex of Formula II as defined above in combination with a pharmaceutically acceptable carrier.

Finally, the present invention is directed to methods for production of compounds of Formula I and Formula II as defined above.

DETAILED DESCRIPTION OF THE INVENTION

In the compounds of Formula I and Formula II, the term "alkyl" means a straight or branched hydrocarbon group having from one to ten carbon atoms and includes, for example, methyl, ethyl, n-propyl, isopropyl, n-butyl, isobutyl, tertiary-butyl, n-pentyl, n-hexyl, n-heptyl, n-octyl, n-nonyl, n-decyl, and the like.

"Alkoxy" is O-alkyl in which alkyl is as defined above.

"Cycloalkyl" means a saturated hydrocarbon ring having three to six carbon atoms and includes cyclopropyl, cyclobutyl, cyclopentyl, cyclohexyl, and the like.

"Halogen" is iodine, bromine, and chlorine.

Certain of the complexes of Formula I and Formula II which contain basic groups are capable of further forming pharmaceutically acceptable acid addition salts. These forms are within the scope of the present invention.

Pharmaceutically acceptable acid addition salts are formed with inorganic and organic acids, such as, for example, hydrochloric, sulfuric, phosphoric, acetic, citric, gluconic, fumaric, methanesulfonic, and the like (see, for example, Berge, S. M., et al., "Pharmaceutical Salts," *Journal of Pharmaceutical Science,* 66, pp. 1-19 (1977)). The acid addition salts of said basic complexes are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

The neutral mixed ligand platinum(II) and platinum(IV) complexes of Formula I and Formula II are restricted to the cis-geometric isomers. Complexes of Formula I and Formula II may also possess asymmetric carbon atoms (optical centers), and thus the racemates as well as the individual enantiomers are also included.

A preferred group of neutral mixed ligand platinum(II) complexes are those of Formula I wherein R is $-(CH_2)_n-$, in which n is an integer from one to three; $R_1$ is hydrogen, carboxyl, an alkyl group of from one to four carbon atoms, or an alkoxy group of from one to four carbon atoms; and $R_2$ and $R_3$ are negatively charged monodentate ligands which may be the same or different and are selected from the group consisting of chloro and bromo or $R_2$ and $R_3$ taken together form a dinegatively charged bidentate ligand selected from the group consisting of

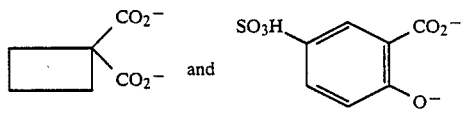

A most preferred group of neutral mixed ligand platinum(II) complexes are those of Formula I wherein $R_1$ is hydrogen, carboxyl, methyl or methoxy.

Particularly valuable are:

[SP-4-2-(cis)]-dichloro(1,4-cyclohexanediamine-N-N')platinum;

[SP-4-2-(cis)]-dichloro(1,3-cyclopentanediamine-N,N')platinum;

[SP-4-2-(cis)]-dichloro(1,4-cycloheptanediamine-N,N')platinum;

[SP-4-2-(cis)]-[1,1-cyclobutanedicarboxylato-2-)-$O^1,O^1$](1,4-cyclohexanediamine-N,N')-platinum; and

[SP-4,2-(cis)]-(1,4-cyclohexanediamine-N,N')[2-hydroxy-5-sulfobenzoato(3-)-$O^1O^2$]platinate (1-), hydrogen.

A preferred group of neutral mixed ligand platinum(IV) complexes are those of Formula II wherein R is $-(CH_2)n-$, in which n is an integer from one to three; and $R_1$ is hydrogen, carboxyl, an alkyl group of from one to four carbon atoms, or an alkoxy group of from one to four carbon atoms.

A most preferred group of neutral mixed ligand platinum(IV) complexes are those of Formula II wherein $R_1$ is hydrogen, carboxyl, methyl, or methoxy.

Particularly valuable are:

[OC-6-22-(cis)]-tetrachloro(1,4-cyclohexanediamine-N,N')platinum; and

[OC-6-33-(cis)]-dichloro(1,4-cyclohexanediamine-N,N')dihydroxyplatinum.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The process of preparing neutral mixed ligand platinum(II) complexes of Formula I is described generally as follows:

A neutral mixed ligand platinum(II) complex of Formula I

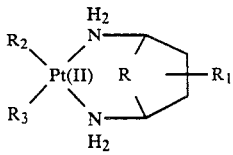

wherein

R is oxygen,

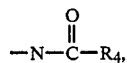

in which $R_4$ is an alkyl group of from one to ten carbon atoms, or $-(CH_2)_n-$, in which n is an integer from one to three;

$R_1$ is hydrogen, carboxyl, an alkyl group of from one to four carbon atoms, an alkyl group of from one to four carbon atoms substituted with alkoxy of from one to four carbon atoms, a cycloalkyl group of from three to six carbon atoms, a hydroxyalkyl group of from one to four carbon atoms, an alkoxy group of from one to four carbon atoms, or benzyl;

and $R_2$ and $R_3$ are negatively charged monodentate ligands which may be the same or different and are selected from the group consisting of chloro, bromo, iodo, nitrato, and acetato or $R_2$ and $R_3$ taken together form a dinegatively charged bidentate ligand selected from the group consisting of sulfato, oxalato,

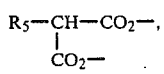

in which $R_5$ is hydrogen, hydroxyl, amino, an alkyl group of from one to four carbon atoms or an aminoalkyl group of from one to four carbon atoms,

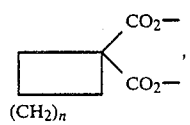

in which n is an integer from one to three, and

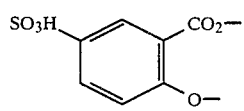

or a pharmaceutically acceptable acid addition salt thereof is prepared by reacting a compound of Formula III

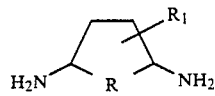

wherein R and $R_1$ are as defined above with potassium tetraiodoplatinate(II) in water at about 60° C. to afford a complex of Formula Ia

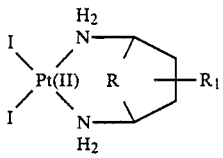

wherein R and $R_1$ are as defined above.

Treatment of a complex of Formula Ia in a conventional manner affords a complex of Formula I.

Thus, treatment of the complex of Formula Ia wherein R and $R_1$ are as defined above with an aqueous solution of silver nitrate precipitates silver iodide and affords a complex of Formula Ib

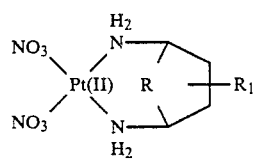

wherein R and $R_1$ are as defined above.

Treatment of the complex of Formula Ia wherein R and $R_1$ are as defined above with an aqueous solution of silver nitrate precipitates silver iodide followed by filtration and addition of a dilute aqueous solution of hydrochloric acid to filtrate affords a complex of Formula Ic

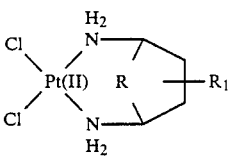

wherein R and $R_1$ are as defined above.

Substitution of a dilute aqueous solution of hydrobromic acid for hydrochloric acid in the previous reaction affords a complex of Formula Id

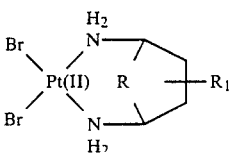

wherein R and $R_1$ are as defined above.

Substitution of an aqueous buffer solution of sodium acetate/acetic acid (pH 5-6) for hydrochloric acid in the previous reaction affords a complex of Formula Ie

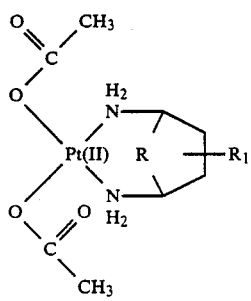

wherein R and R₁ are as defined above.

Treatment of the complex of Formula Ia wherein R and R₁ are as defined above with an aqueous solution of silver sulfate precipitates silver iodide and affords a complex of Formula If

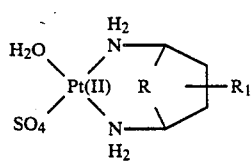

wherein R and R₁ are as defined above.

Treatment of the complex of Formula If wherein R and R₁ are as defined above with a solution of barium hydroxide to remove the sulfate, followed by filtration and reaction with a solution of oxalic acid (pH adjusted to 6 with sodium hydroxide) affords a complex of Formula Ig

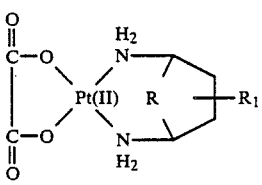

wherein R and R₁ are as defined above.

Substitution of

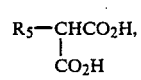

in which $R_5$ is as defined above, for oxalic acid in the previous reaction affords a complex of Formula Ih

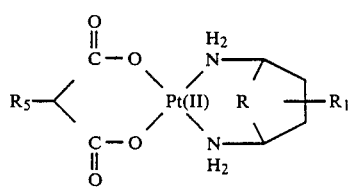

wherein R, R₁, and R₅ are as defined above.

Substitution of

(pH adjusted to 5-6) in which n is as defined above, for the solution of oxalic acid in the previous reaction affords a complex of Formula Ii

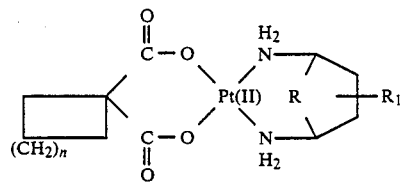

wherein R, R₁, and n are as defined above.

Substitution of

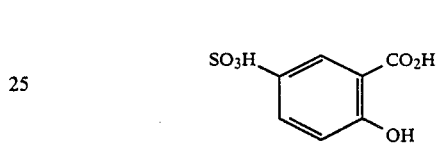

for oxalic acid in the previous affords a complex of Formula Ij

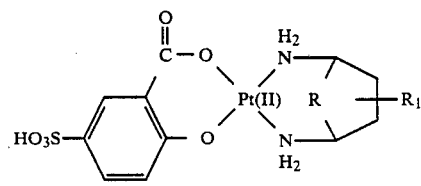

where in R and R₁ are as defined above.

Potassium tetraiodoplatinate is prepared in situ from potassium tetrachloroplatinate and potassium iodide in the conventional manner.

Compounds of Formula III are either known or capable of being prepared by methods known in the art.

The process of preparing neutral mixed ligand platinum(IV) complexes of Formula II is described generally as follows:

A neutral mixed ligand platinum(IV) complex of Formula II

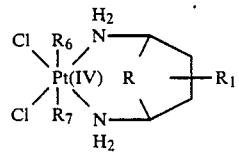

wherein
R is oxygen,

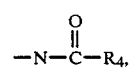

in which $R_4$ is an alkyl group of from one to ten carbon atoms, or

—$(CH_2)_n$—, in which n is an integer from one to three;

$R_1$ is hydrogen, carboxyl, an alkyl group of from one to four carbon atoms, an alkyl group of from one to four carbon atoms substituted with alkoxy of from one to four carbon atoms, a cycloalkyl group of from three to six carbon atoms, a hydroxyalkyl group of from one to four carbon atoms, an alkoxy group of from one to four carbon atoms, or benzyl; and $R_6$ and $R_7$ are negatively charged monodentate ligands which may be the same or different and are selected from the group consisting of chloro, bromo, hydroxyl, and nitrato or a pharmaceutically acceptable acid addition salt thereof, is prepared by reacting a complex of Formula Ic

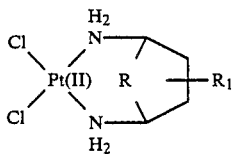

wherein R and $R_1$ are as defined above.

Treatment of a complex of Formula Ic in a conventional manner affords a complex of Formula II. Thus, treatment of a complex of Formula Ic in a 15% aqueous solution of hydrogen peroxide and concentrated chloric acid solution at about room temperature to about 60° C. affords a complex of Formula IIa

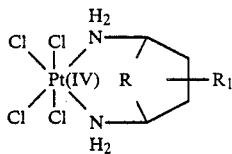

wherein R and $R_1$ are as defined above.

Treatment of the complex of Formula Ic wherein R and $R_1$ are as defined above in water with a 15% aqueous solution of hydrogen peroxide while warming at about room temperature to about 60° C. affords a complex of Formula IIb

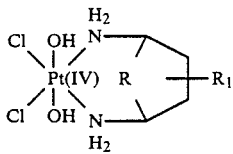

wherein R and $R_1$ are as defined above.

Treatment of the complex of Formula IIb wherein R and $R_1$ are as defined above in water with an aqueous solution of nitric acid affords a complex of Formula IIc

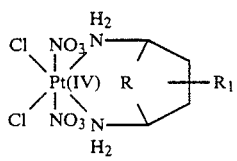

wherein R and $R_1$ are as defined above.

The neutral mixed ligand platinum II complexes of Formula I and platinum IV complexes of Formula II can be prepared and administered in a wide variety of oral and parenteral dosage forms. The complexes of Formula I and Formula II are valuable anticancer agents.

The data in the tables shows the antineoplastic activity of a representative compound of the present invention. Thus, in Table 1, the efficacy of Example I of the present invention compared to [SP-4-2-(1R-trans)]-dichloro(1,2-cyclohexanediamine-N,N')platinum[Pt(-trans-l-DACH)Cl$_2$] is shown as measured against strains of L1210 and P388 cell lines which were selected for their resistance to cis-diaminedichloroplatinum(II) (cisplatin). ID$_{50}$ values were determined for each compound shown in the table as measured against the normal L1210 and P388 cell lines, as well as against L1210 and P388 cell lines which were selected for their resistance to cisplatin at a concentration of 4 μg/ml. ID$_{50}$ values are the concentration of complex required to inhibit the in vitro growth of treated cells to a level of 50% of that for untreated cells over a 72-hour period. The cell lines are suspended in appropriate media at a concentration which results in the cells remaining in log phase growth throughout the treatment period. Serially diluted drug is added to duplicate wells containing the cell growth. After 72 hours of incubation of the cell lines in 5% CO$_2$, the cells are counted and the ID$_{50}$ values determined.

Resistance ratio values shown in Table 1 were calculated by dividing the ID$_{50}$ values against the resistant cell lines by the ID$_{50}$ values against the normal cell lines. The resistance ratio values shown in the table indicate a measure of the degree of resistance of the cell line to a particular drug. Thus, the higher the resistance ratio, the less effective is the drug against the cisplatin-resistant cell line.

Moreover, the complexes of the present invention demonstrate activity against the L1210 and P388 murine leukemia cell lines. The screening tests employing these cell lines are described in Geran et al., "Protocols for Screening Chemical Agents and Natural Products Against Animal Tumors and Other Biological Systems," *Cancer Chemotherapy Reports*, Part 3, Vol. 3, No. 2, pages 1–85 (1972). The L1210 and P388 screening methods have been cited as the best tools for predicting clinical utility of drugs in the treatment of human solid tumors as well as human leukemias and lymphomas (Venditti, "Relevance of Transplantable Animal-Tumor Systems to the Selection of New Agents for Clinical Trial," Pharmacological Basis of Cancer Chemotherapy, Williams & Williams Pub. Co. (1975)).

In Table 2, the ratio of median survival time of laboratory mice which had been treated with the test compound to untreated control animals is expressed as a percentage (%T/C values). Laboratory mice were implanted intraperitonealy with the L1210 murine leukemia cell line on Day 0 and treated with intraperitoneal injections of representative platinum complexes of the present invention on Days 3 and 7 at the dosages indicated. Data for the prior art complex cisplatin is included for comparison.

The antitumor activity of Example 1 is superior to cisplatin both in potency and response according to in vitro and in vivo test results. Thus, Example 1 is equally effective or superior to cisplatin against the parent L1210 and P388 leukemia cell lines in vivo. While Example 1 shows some degree of cross resistance to cisplatin in vitro and in vivo, it is more effective than cisplatin against cisplatin-resistant cells in vitro and in vivo. Additionally, Example 1 shows only a fourfold cross resistance to Pt(DACH)Cl$_2$-resistant L1210 cells in culture while [Pt(trans-l-DACH)Cl$_2$] shows a 77-fold resistance to the same system, i.e., Example 1 does not seem to be acting like a Pt(DACH) complex.

Moreover, Example 1 is ten times more soluble in saline than and can be administered as a homogeneous solution in saline as opposed to a slurry in the case of [Pt(trans-l-DACH)Cl$_2$].

TABLE 1

In Vitro Cytotoxicity of
[SP-4-2-(cis)]-Dichloro(1,4-cyclohexanediamine-$\underline{N},\underline{N}'$)-
Platinum (Example I), ID$_{50}$ (μg/ml)

|  | Cisplatin | [Pt(trans-λ-DACH)Cl$_2$]$^a$ | Example 1 |
|---|---|---|---|
| L1210S | 0.375 | 0.059 | 0.248 |
| L1210PtR4 | 7.84 (21)$^b$ | 0.161 (2.7) | 1.21 (4.9) |
| L1210DDP5 | 4.11 (11) | 0.164 (2.8) | 0.663 (2.7) |
| L1210DACH | 0.52 (1.4) | 4.57 (77) | 1.08 (4.3) |
| P388S | 0.128 | 0.077 | 0.047 |
| P388Pt4 | 10.0 (78) | 0.83 (10.8) | 1.43 (30) |

$^a$[SP-4-2-(1 R-trans)]-dichloro(1,2-cyclohexanediamine-$\underline{N},\underline{N}'$)platinum.
$^b$Fold resistance.

TABLE 2

In Vivo Cytotoxicity of
[SP-4-2-(cis)]-dichloro(1,4-cyclohexanediamine-
$\underline{N},\underline{N}'$)platinum (Example 1)

| Compound | Dose$^b$ (IP, mg/kg/injection) | Weight Change (grams) | MLS (days)$^d$ | % T/C$^e$ | 60 Day Survivors | Log$_{10}$ Kill Gross | Log$_{10}$ Kill Net |
|---|---|---|---|---|---|---|---|
| | | L-1210 Leukemia$^a$ | | | | | |
| Example 1 | 6.3 | | 10.7 | 101 | 0/6 | 0.1 | −1.9 |
| | 3.0 | −4.8 | 21.5 | 203 | 1/6 | 11.5 | 3.1 |
| | 1.5 | 0.6 | 23.0 | 217 | 0/6 | 13.1 | 4.6 |
| | 0.8 | 3.2 | 13.0 | 130 | 0/6 | 3.4 | −1.5 |
| | 0 | | 10.6 | | 0/6 | | |
| Cisplatin$^c$ | 6.0 | −1.9 | 18.5 | 175 | 1/6 | 8.3 | −0.1 |
| | 4.0 | 1.0 | 19.5 | 184 | 1/6 | 9.4 | 0.9 |
| | | L-1210/Pt Leukemia (Cisplatin Resistant) | | | | | |
| Example 1 | 0 | | 10.2 | | 0/12 | | |
| | 6.3 | | 10.3 | 101 | 0/6 | 0.1 | −2.7 |
| | 3.0 | −4.3 | 17.0 | 167 | 2/6 | 5.5 | −1.0 |
| | 1.5 | 1.9 | 15.7 | 154 | 0/6 | 4.5 | −1.7 |
| | 0.8 | 3.7 | 12.8 | 126 | 0/6 | 2.1 | −2.2 |
| Cisplatin$^c$ | 6.0 | −3.7 | 12.0 | 118 | 0/6 | 1.5 | −2.4 |
| | 4.0 | | 11.1 | 109 | 0/6 | 0.7 | −2.5 |

| Compound | Dose$^g$ (IP, mg/kg/injection) | Weight Change (grams) | MLS (days)$^d$ | % T/C$^e$ | 60 Day Survivors | Log$_{10}$ Kill Gross | Log$_{10}$ Kill Net |
|---|---|---|---|---|---|---|---|
| P-388 (Lymphocytic Leukemia)$^f$ | | | | | | | |
| | | P-388/Pt (Cisplatin Resistant)$^f$ | | | | | |
| Example 1 | 3.7 | | | 234 | | | 5.4 |
| Cisplatin$^c$ | 5.0 | | | 261 | | | 6.8 |
| Example 1 | 3.7 | | | 177 | | | 1.9 |
| Cisplatin$^c$ | 5.0 | | | 132 | | | −1.5 |

$^a$Inoculum: 10,000 cells (IP)
$^b$Schedule: Days 3, 7, 11
$^c$Positive control: Cis Pt(NH$_3$)$_2$Cl$_2$
$^d$Median life span
$^e$Best responses
$^f$Inoculum = IP
$^g$Schedule: Days 1, 5, 9

For preparing pharmaceutical compositions from the complexes of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from 5 to 10 to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can also be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg, preferably 1 mg to 10 mg, according to the particular application and the potency of the active component. The composition can, if desired, also contain other compatible therapeutic agents.

In therapeutic use as antineoplastic agents, the complexes utilized in the pharmaceutical method of this invention are administered to the patient preferably in daily intravenous doses of from 10 to 100 mg/m$^2$ of body area on a regimen of from one to seven days, repeated as needed after a hiatus of from two to six weeks. The dosages and dosage regimen, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting example illustrates the inventors' preferred method for preparing the complexes of the invention.

EXAMPLE 1

[SP-4-2-(c-is)]-Dichloro(1,4-cyclohexanediamine-N,N')-platinum

A solution of potassium tetraiodoplatinate(II), 400 ml (prepared in situ from 5 g (12 mmol) of potassium tetrachloroplatinate in 350 ml of water* and 14.62 g (88.1 mmol) of potassium iodide in 500 ml of water) and 400 ml of cis-1,4-diaminocyclohexane in water (prepared from 2.25 g (12 mmol) of cis-1,4-diaminocyclohexane dihydrochloride and 24 ml (24 mmol) of 1M sodium hydroxide) are simultaneously pumped at equal rates (2.6 ml/minute) via a peristalic pump into a 3-liter flask containing 250 ml of water maintained at 60° C. The flask is stirred vigorously via an external mechanical stirrer as the reagents are delivered over 2.6 hours. The reaction mixture is maintained at 60° C. during delivery of the reagents and for 0.5 hours after delivery. The reaction is cooled to ambient temperature, filtered through a medium porosity sintered glass filter (material adhering to the inside surface of the reaction flask is loosened via agitation in an ultrasonic bath) to afford about 5.7 g of the iodoamine intermediate. The iodoamine intermediate is slurried in water and a solution of silver nitrate, 3.8 g (110% of the stoichiometric amount) in water is added and the mixture heated at 60° C. with stirring for 30 to 60 minutes, allowed to stir at ambient temperature overnight, and filtered (0.2μ filter) to afford a clear water white filtrate. Excess silver cation is removed as silver chloride via several additions (followed by filtration after each addition) of 1M hydrochloric acid. The silver-free filtrate (300 to 400 ml) is cooled to 0° C., concentrated in vacuo to about 50 ml, 4 ml (48 mmol) of 12N hydrochloric acid (twice the stoichiometric amount of Cl$^-$ ion) is added, the mixture warmed to about 45° C. for 15 minutes, and then cooled in an ice bath to crystallize the desired product. The pale yellow product is filtered, washed with 0.1N hydrochloric acid (0° C.) and ethanol (0° C.), dried by suction in air, and then in vacuo at 50° C. for two hours to afford 0.8 g of product. Dissolution of the previous material in dimethylformamide (30 mg/ml) followed by the addition of two volumes of 0.1N hydrochloric acid affords 0.51 g of [SP-4-2(cis)]-dichoro(1,4-cyclohexanediamine-N,N')-platinum.

*Deaerated water (argon) was used throughout this preparation.

Anal. $C_6H_{14}N_2Cl_2$ Pt Calc.: C, 18.96; H, 3.71; N, 7.37; Cl, 18.65. Found: C, 18.94; H, 3.71; N, 7.37; Cl, 18.96. $^{195}$Pt—NMR (DMF—d$_7$) ppm (parts per million)—587. $^{13}$C—NMR(D$_2$O) ppm 24.41 (CH$_2$), 50.38 (CH). $^1$H—NMR (D$_2$O) δ5.46 (NH$^2$), 3.12 (CH), 1.84 (CH$_2$).

MS (FABS) (mass spectrum—fast atom bombardment spectrum) molecular ion 380.1

UV (ultraviolet light $\lambda_{max}$=279 nm (E=113 M$^{-1}$ cm$^{-1}$). Ratio of $$\frac{\lambda (270)}{\lambda 363} = 3.19$$

We claim:

1. A neutral ligand platinum (II) complex of formula I

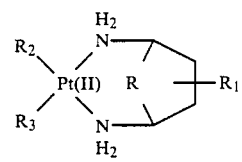

or a pharmaceutically acceptable acid addition salt thereof, wherein R is
- —(CH$_2$)$_n$—, in which n is an integer from two to three;
- R$_1$ is hydrogen, carboxyl, an alkyl group of from one to four carbon atoms, an alkyl group of from one to four carbon atoms substituted with alkoxy of from one to four carbon atoms, a cycloalkyl group of from three to six carbon atoms, a hydroxyl group of from one to four carbon atoms, an alkoxy group of from one to four carbon atoms, or benzyl; and $R_2$ and $R_3$ are negatively charged monodentate ligands which may be the same or different and are selected from the group consisting of chloro, bromo, iodo, nitrato, and acetato or $R_2$ and $R_3$ taken together form a dinegatively charged bidenate ligand selected from the group consisting of sulfato, oxalato,

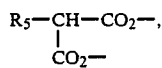

in which $R_5$ is hydrogen, hydroxyl, amino, an alkyl group of from one to four carbon atoms or an aminoalkyl group of from one to four carbon atoms,

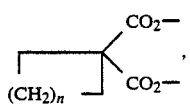

in which n is an integer from one to three, and

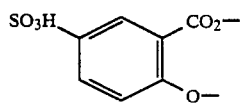

2. A neutral ligand platinum(II) complex as defined in claim 1 wherein R is $-(CH_2)_n-$, in which n is an integer from two to three; $R_1$ is hydrogen, carboxyl, an alkyl group of from one to four carbon atoms or an alkoxy group of from one to four carbon atoms; and $R_2$ and $R_3$ are negatively charged monodentate ligands which may be the same or different and are selected from the group consisting of chloro and bromo or $R_2$ and $R_3$ taken together form a dinegatively charged bidentate ligand selected from the group consisting of

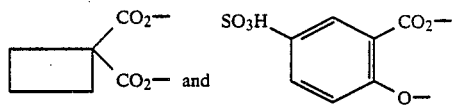

3. A neutral ligand platinum(II) complex as defined in claim 2 wherein $R_1$ is hydrogen, carboxyl, methyl, or methoxy.

4. A neutral ligand platinum(II) complex as defined in claim 3 having the same [SP-4-2-(cis)]-dichloro(1,4-cyclohexanediamine-N,N')platinum.

5. A pharmaceutical composition for inhibiting the growth of neoplasms in mammals comprising an antineoplastically effective amount of a neutral ligand platinum(II) complex as defined in claim 1 in combination with a pharmaceutically acceptable carrier.

6. A method of inhibiting the growth of neoplasms in mammals comprising administering to said mammal an effective amount of a neutral ligand platinum(II) complex as defined in claim 1 in combination with a pharmaceutically acceptable carrier.

* * * * *

UNITED STATES PATENT AND TRADEMARK OFFICE
CERTIFICATE OF CORRECTION

PATENT NO. : 4,999,444
DATED : March 12, 1991
INVENTOR(S) : J. D. Hoeschele, et al.

It is certified that error appears in the above—identified patent and that said Letters Patent is hereby corrected as shown below:

In column 17, Claim 1, line 2 delete "hydroxyl" and insert --hydroxyalkyl--.

In column 18, Claim 4, line 21 delete "same" and insert --name--.

Signed and Sealed this

Tenth Day of November, 1992

*Attest:*

DOUGLAS B. COMER

*Attesting Officer*      *Acting Commissioner of Patents and Trademarks*